(12) United States Patent
Kamada et al.

(10) Patent No.: US 8,728,539 B2
(45) Date of Patent: May 20, 2014

(54) METHOD OF ENHANCING INTESTINAL PINOCYTOSIS OF IMMUNOGLOBULINS IN POSTNATAL DOMESTIC MAMMALS

(75) Inventors: Hachiro Kamada, Tsukuba (JP); Itoko Nonaka, Tsukuba (JP)

(73) Assignee: Incorporated Administrative Agency, National Agriculture and Bio-Oriented Research Organization, Tsukuba-shi (JP)

( * ) Notice: Subject to any disclaimer, the term of this patent is extended or adjusted under 35 U.S.C. 154(b) by 1453 days.

(21) Appl. No.: 12/152,080

(22) Filed: May 12, 2008

(65) Prior Publication Data

US 2008/0248027 A1    Oct. 9, 2008

Related U.S. Application Data

(63) Continuation-in-part of application No. 11/195,455, filed on Aug. 2, 2005, now abandoned.

(30) Foreign Application Priority Data

Dec. 7, 2004 (JP) ................. 2004-354190

(51) Int. Cl.
*A61K 33/04* (2006.01)
*A61K 35/20* (2006.01)
*A61K 39/00* (2006.01)
*A61K 39/395* (2006.01)
*A23K 1/175* (2006.01)
*A23K 1/18* (2006.01)

(52) U.S. Cl.
USPC ............. 424/702; 424/130.1; 424/157.1; 424/438; 424/442; 424/535

(58) Field of Classification Search
CPC ....... A61K 33/04; A61K 35/20; A61K 39/00; A61K 39/39508; A23K 1/175; A23K 1/1813
USPC ........... 424/130.1, 157.1, 438, 442, 535, 702
See application file for complete search history.

(56) References Cited

U.S. PATENT DOCUMENTS

| | | | |
|---|---|---|---|
| 5,785,990 A | 7/1998 | Langrehr | |
| 5,846,569 A | 12/1998 | Anderson | |
| 6,667,063 B2 * | 12/2003 | Crum | 424/535 |
| 2003/0064116 A1 | 4/2003 | Crum | |

FOREIGN PATENT DOCUMENTS

| | | |
|---|---|---|
| JP | 61-289845 | 12/1986 |
| JP | 03-216156 | 9/1991 |
| JP | 10-070960 | 3/1998 |
| JP | 2002-508317 | 3/2002 |
| WO | 9930700 | 6/1999 |

OTHER PUBLICATIONS

K.J. Jenkins and M. Hidiroglou, "Tolerance of the Preruminant Calf for Selenium in Milk Replacer", Journal of Dairy Science, 1986, 69, 1865-1870.*
Merrick's Inc., "Plas/Magic Milk Fortifier", Aug. 2000, http://www.merricks.com/plasmagic.html.
Hirotaka Kasuya, Koichiro Uchida, Hiromichi Ohtsuka, Takatsugu Hattori, Shonyu Management wo kangaeru, 2001, vol. 19, No. 3, (Japanese text with an English abstract).
Julian E. Spallholz et al., "Infection and Immunity, Enhanced Immunoglobulin M and Immunoglobulin G Antibody Titers in Mice Fed Selenium", Journals.ASM.org, Nov. 1973, vol. 8, No. 5, p. 841-842, American Society for Microbiology.
"FDA selenium regulations finalized", JAVMA, vol. 211, No. 10, p. 1224, Nov. 15, 1997.
R.J. Van Saun, "Rational approach to selenium supplementation essential", Feedstuff, vol. 62, p. 15-17, 1990.
"Nutrient Requirements of Dairy Cattle", National Research Council,, Sixth Revised Edition, p. 87, National Academic Press, 1988.

* cited by examiner

*Primary Examiner* — John Pak
*Assistant Examiner* — Nathan W Schlientz
(74) *Attorney, Agent, or Firm* — Fox Rothschild LLP

(57) ABSTRACT

Disclosed is a method of enhancing absorption (pinocytosis efficiecy) of immunoglobulins administered to postnatal domestic mammals (e.g., bovine) by using selenium. As an example of a selenium compound added, sodium selenite is particularly effective.

2 Claims, 7 Drawing Sheets

Occurrences of infectious diseases and insufficient growth (B)

Healthy cattle

METHOD OF ENHANCING INTESTINAL PINOCYTOSIS OF IMMUNOGLOBULINS IN POSTNATAL DOMESTIC MAMMALS

CROSS-REFERENCE TO RELATED APPLICATIONS

The application is a continuation-in-part (CIP) of U.S. patent application Ser. No. 11/195,455, filed Aug. 2, 2005 now abandoned.

BACKGROUND OF THE INVENTION

1. Field of the Invention

The present invention relates to a method of enhancing pinocytosis of immunoglobulins in postnatal domestic mammals (e.g., bovine).

2. Description of the Related Art

An immunoglobulin is a protein, which has a role in eliminating pathogenic microbes and is essential to mammals. In particular, postnatal calves cannot produce immunoglobulins on their own and cannot protect themselves from infectious diseases without intaking immunoglobulins from the outside sources. Since the first milking colostrum secreted post-parturition by maternal cows contains a high concentration of immunoglobulins, calves normally acquire immunoglobulins by ingestion of such colostrum. However, the absorption capacity of immunoglobulins (pinocytosis) in the small intestines of calves decreases as a function of time post-parturition and almost comes to a nil within 24 hours post-parturition. Because of this phenomenon, the absorption of immunoglobulins is normally accomplished by earlier administration of colostrum to postnatal calves. In this regard, the important points in administering colostrum are as follows: (1) the timing of administering colostrum, (2) the administration amount of colostrum, and (3) the quality of colostrum. As to these conditions, they are described in detail in "Management of Colostrum," Journal of Clinical Veterinary Medicine, Vol. 19, No. 3 (2001), pp. 18-38. However, there is no method of enhancing pinocytosis efficiecy in postnatal mammals until now.

However, there are many cases in which the above supply conditions cannot be met on account of various reasons. For example, there may be cases of an insufficient amount of colostrum for primiparous cows or an insufficient amount of immunoglobulins in colostrum. The absorption capacity of immunoglobulins in calves may change due to stress or temperature. For these reasons, it cannot be said that the amount of absorption of immunoglobulins in postnatal domestic mammals is sufficient under these circumstances, and the rate of occurrences of infectious diseases in immature calves and the attrition rate have not come down to the satisfactory levels. Accordingly, in order to further enhance resistance of calves against infectious diseases, there remains a need for enhancing absorption capacity of immunoglobulins (pinocytosis efficiency) in postnatal domestic mammals such as calves.

SUMMARY OF THE INVENTION

The relations between the constituents contained in colostrum and the absorption capacity of immunoglobulins in calves have not yet been clarified. The roles of minerals in mammals are gradually been elucidated, and the important roles of certain types of minerals in body have been shown. It is known that for example selenium possesses anti-cancerous activities and activates thyroid hormones. The inventors herein have been looking at the roles of selenium in bovine and have found that the enhancement of the absorption capacity of immunoglobulins is accomplished in the intestines of calves by administration of selenium. In this regard, the absorption of immunoglobulins at the intestinal tracts occurs by pinocytosis of epithelial cells of the intestinal tracts. Selenium is thought to somehow facilitate this pinocytosis process.

Accordingly, the present invention provides a method of enhancing absorption of immunoglobulins (pinocytosis efficiency) in the intestines of postnatal domestic mammals by way of administration of selenium, thereby improving resistance to infectious diseases in postnatal domestic mammals and reducing the attrition rate thereof.

DETAILED DESCRIPTION OF THE PREFERRED EMBODIMENTS

Hereinafter, the embodiments of the present invention will be described in particular details.

Figure 1:
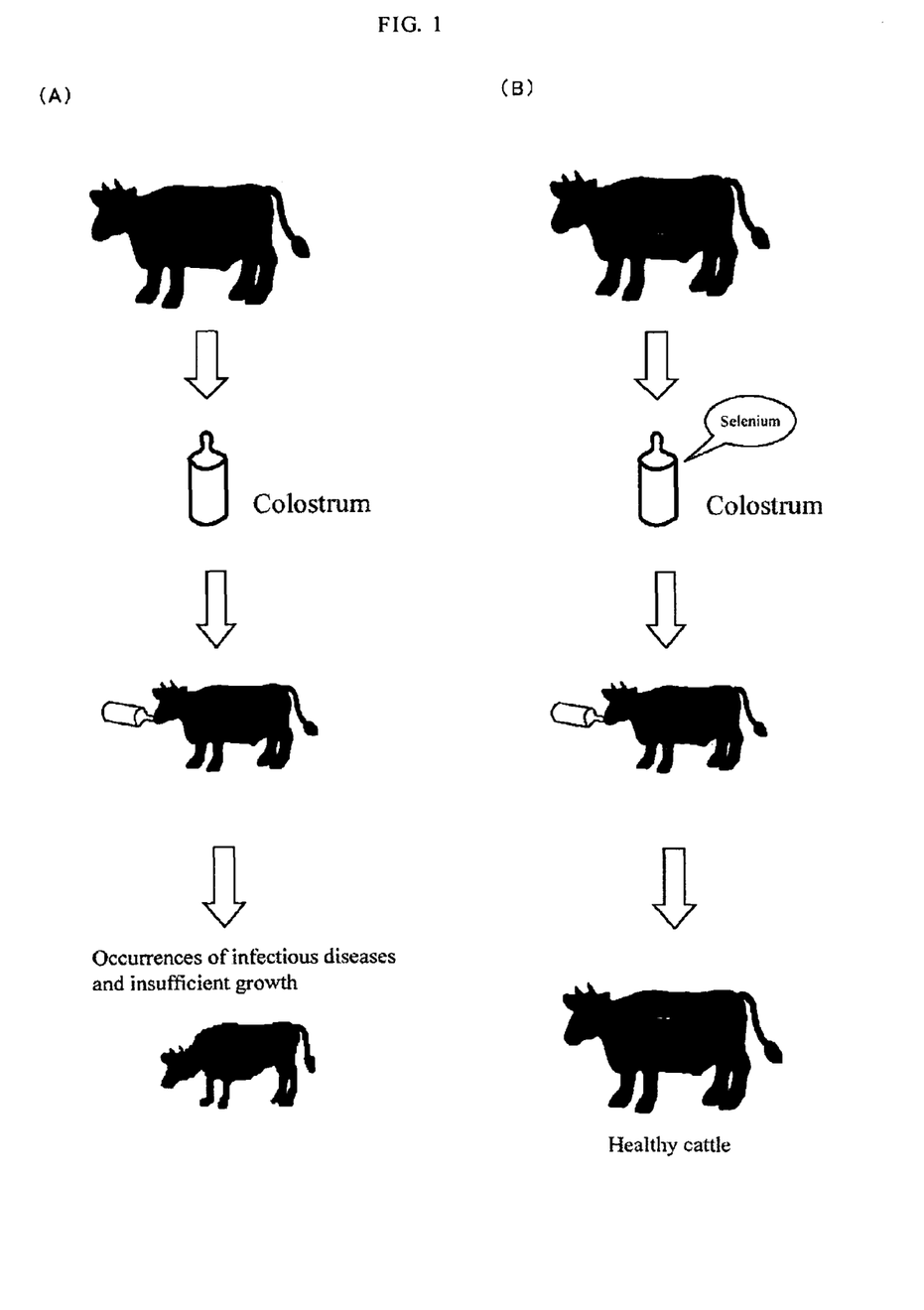
FIG. 1 is a schematic diagram of one of the embodiments of the present invention.

FIG. 1 is a schematic diagram of one of the embodiments of the present invention. As an illustration in FIG. 1(A), where normal colostrum is administered to calves, if the intake thereof is not sufficient, infectious diseases and insufficient growth are more likely before maturity, leading to a higher death rate of calves in general. Meanwhile, as in the present invention, where selenium is administered to calves prior to or at immunoglobulin feeding, the absorption of immunoglobulins (pinocytosis) in calves is enhanced, leading to a higher rate of healthy calves in maturity.

One of the embodiments of the present invention is a method of enhancing absorption of immunoglobulins (pinocytosis) in postnatal domestic mammals (e.g., calves), which comprises an administration of a selenium compound so that the concentration of selenium in feed is 1 to 5 ppm. Immunoglobulins refer to proteins, which are synthesized and secreted by B lymphocytes, and which possess the functions of identifying and eliminating pathogenic microbes. Examples of immunoglobulins include A, G, and M types. Immunoglobulins A (IgA), which exist in salvia, digestive fluid, and phlegm, play an important role in the defense system of mucous membranes. Immunoglobulins G (IgG), which exist in blood, possess for example the functions of fighting against invading microbes or foreign substances in body, and activating protein complements. Immunoglobulins M (IgM), which appear at the outset of antigenic stimulation, also have the functions of fighting against microbes or foreign substances, and activating protein complements. Here, "domestic mammals" include all forms of life acquiring immunoglobulins by postpartum feeding from maternal sources, e.g., human, bovine, porcine, and equine.

Selenium is essential to mammals, and the deficiencies of selenium result in a variety of pathological symptoms. On the other hand, selenium can be toxic as well, and an excessive consumption may result in other forms of pathological symptoms. Accordingly, the selenium concentration used in this method is at 1 to 5 ppm, or preferably 2.5 to 3.5 ppm. If the selenium concentration is less than the above lower limit, the absorption of immunoglobulins (pinocytosis efficiency) is insufficient, and if the mineral content is more than the above upper limit, there may be harmful effects on mammals due to excessive selenium.

Selenium compound(s) used in this method can be one or more compounds selected from a group consisting of sodium selenite, sodium selenate, potassium selenite, and potassium selenate. Selenium is essential in the synthesis of enzymes (glutathione peroxidase), which detoxify activated oxygen, and is an important antioxidant nutrient for life support. In particular, selenium is known to have the functions of preventing cancer and regulating thyroid hormones. In regard to the absorption of immunoglobulins (pinocytosis) at the intestinal tracts, selenium is thought to somehow facilitate the pinocytosis process occurring at the intestinal tracts by way of epithelial cells.

Other examples of compounds containing selenium include compounds of selenium with an oxidation number of −2, such as $Na_2Se$, $CaSe$, $ZnSe$, $CdSe$, $Cu_2Se$, $Ag_2Se$; organic selenium compounds, such as dimethylselenide, selenocystine, selenomethionine; selenate; and selenite. Selenate compounds are compounds of selenium with an oxidation number of 6, and include sodium selenate ($Na_2SeO_4$), and potassium selenate ($K_2SeO_4$). Selenite compounds are compounds of selenium with an oxidation number of 4, and include sodium selenite ($Na_2SeO_3$), and potassium selenite ($K_2SeO_3$). In particular, since sodium selenite in powder form is easily soluble in water, it can be suitably added to colostrum as an additive herein.

Colostrum generally refers to milk secreted within one week post-parturition by maternal mammals. With respect to colostrum, the first milk secreted post-parturition is rich in immunoglobulins, and after the second milking, its immunoglobulin concentration rapidly decreases. Accordingly, it is preferable to use the first milking colostrum post-parturition. Moreover, since the colostrum secreted by a non-primiparous mother contains a higher concentration of immunoglobulins than that secreted by a primiparous mother, the former colostrum is preferable.

Another aspect of the present invention relates to a method of enhancing absorption of immunoglobulins (pinocytosis) in postnatal domestic mammals, which comprises administering a selenium compound to a postnatal domestic mammal prior to or at feeding of immunoglobulin source. Recommended concentration of selenium in feed is 1 to 5 ppm, or more preferably 2.5 to 3.5 ppm. As the absorption capacity of immunoglobulins (pinocytosis) in postnatal domestic mammals decrease drastically postpartum as a function of time, the administration of selenium should be made within 12 hours postpartum, or preferably 3 hours postpartum.

The above selenium compound and immunoglobulin source are ordinarily administered to mammals by oral administration, etc. Of course, colostral feeding is available as well. In such cases, the first feeding of colostrum is provided at 0.3 to 3 liters, or preferably at 0.85 to 1.15 liters. The upper and lower limits are generally available from the Japanese Husbandry Standards, or the Nutrient Requirements of Dairy Cattle (7th rev. ed., pp. 221). In particular, the Japanese Husbandry Standards recommend feeding of colostrum of 1-2 liters within 4 hours postpartum, and 2 liters within 4-6 hours postpartum. Further, the Nutrient Requirements of Dairy Cattle recommend feeding of colostrum of at least 3 liters within one hour postpartum.

Still another embodiment of the present invention is a method of enhancing absorption of immunoglobulins (pinocytosis) in postnatal domestic mammals, wherein said administration involves a first feeding of said selenium compound within 3 hours postpartum and following feeding of the immunoglobulin source within 12 hours postpartum. As for the initial supplying of selenium compound, it is necessary that such supply be made within 3 hours postpartum in order to enhance pinocytosis efficiency in postnatal domestic mammals. As for the second-round of administration of a immunoglobulin source within 12 hours postpartum, it is carried out to supplement absorption of immunoglobulins therein.

EXAMPLE

Hereinafter, the present invention will be described by using an example, but is not to be limited by such example.

In the example, colostrum added with selenium was administered to one of the two calves (Holstein types) in a pair, and colostrum without selenium was administered to the other calf. A total of 32 pairs of calves were employed for experimental purposes. For equalizing the experimental conditions of these two sets of calves, they were selected based on their proximities in body weight. The body weights ranged from 30.8-56.9 kg, and the differences between in body weight within a pair were less than 2.5 kg.

As a supply source of selenium, sodium selenite was used. In order to avoid different absorption rates of immunoglobulins based on different types of colostrum, the same amounts of colostrum milked from the same source were fed to these two calves in a pair. The colostrums fed (frozen for preservation) were of the four types as follows: the first milking post-parturition (Colostrum 1), the second milking post-parturition (Colostrum 2), the third milking post-parturition (Colostrum 3), and the fourth milking post-parturition (Colostrum 4). 2 liters of Colostrum 1 (1 L×2 bottles) were taken, and for the rest, 4 liters (2L×2 bottles) were taken, respectively. 1 liter of Colostrum 1 within 2 hours post-parturition was fed, and then 2 liters of Colostrum 2, 3 and 4 were fed, respectively 12, 24 and 36 hours post-parturition. The concentrations of immunoglobulins in the colostrums used were 24.3-129.0 mg/ml, and those of selenium were 0.06-0.1 ppm (before adding selenium). The concentrations of immunoglobulins G (IgG) in plasma of calves 24 hours post-parturition were measured by means of radial immuno-diffusion (RID). The experiments as above were carried out while varying the selenium content based on the number of addition of selenium, i.e., (1) adding selenium only to Colostrum 1 (1.0-5.0 ppm), and (2) adding selenium to all four types of colostrum (0.2-4.0 ppm). As a reference, a graph showing the selenium concentrations in plasma after administration is provided in FIG. 4.

The results of the experiments are set forth in the tables as below:

TABLE 1

| Administration of Se (1x) | Body weight (kg) | IgG in Plasma (mg/ml) |
|---|---|---|
| Addition of 1 ppm of Se | 42.3 | 17 |
| No addition | 43 | 14.9 |
| (Average of 3 calves) | | |
| Addition of 2 ppm of Se | 39.2 | 16 |
| No addition | 40.1 | 15.8 |
| (Average of 3 calves) | | |
| Addition of 3 ppm of Se | 44.2 | 21.5 |
| No addition | 44.4 | 17.8 |
| (Average of 6 calves) | | |
| Addition of 4 ppm of Se | 42.2 | 17.4 |
| No addition | 41.9 | 14.9 |
| (Average of 4 calves) | | |
| Addition of 5 ppm of Se | 43.5 | 23 |
| No addition | 43 | 22.6 |
| (Average of 4 calves) | | |

Table 1 shows the body weights and the amounts of IgG in plasma in calves under experiment. Measurements are average values of calves within a test set, each set ranging from 3 to 6 pairs of calves. Selenium was added only once to the first colostrum feed (1×).

TABLE 2

| Administration of Se (4x) | Body weight (kg) | IgG in Plasma (mg/ml) |
|---|---|---|
| Addition of 0.2 ppm of Se | 42.1 | 25.7 |
| No addition | 46.0 | 20.1 |
| (Average of 3 calves) | | |
| Addition of 1.0 ppm of Se | 43.6 | 32.9 |
| No addition | 43.5 | 30.0 |
| (Average of 5 calves) | | |
| Addition of 5.0 ppm of Se | 40.9 | 24.6 |
| No addition | 42.2 | 28.1 |
| (Average of 4 calves) | | |

Table 2 shows the data set for cases, in which colostrum feeds with or without additions of selenium were fed four times to calves under experiment.

Figure 2:
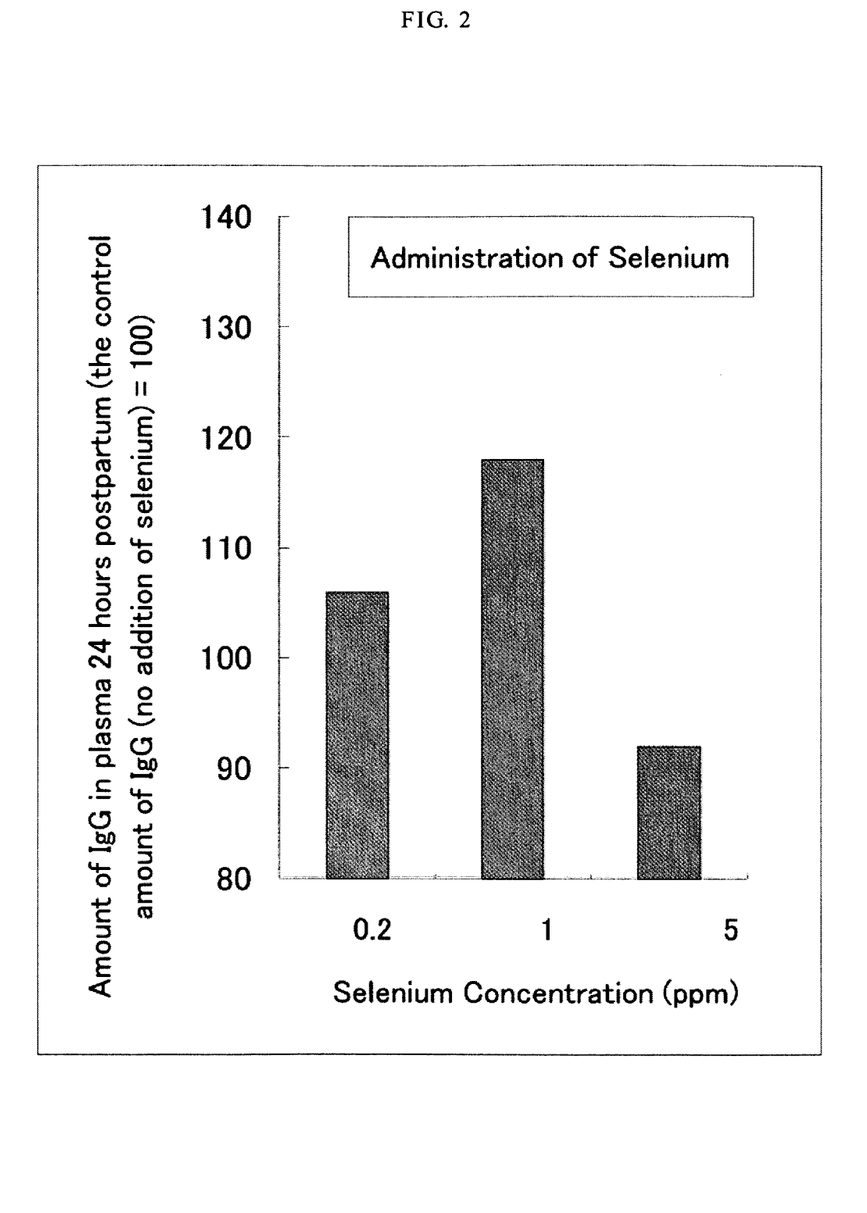
FIG. 2 is a comparative graph, which shows the IgG amount in plasma of calves administered with colostrum with selenium, in which 100 represents the IgG concentration in plasma of calves administered with colostrum without selenium. To calves administered with colostrum with selenium, selenium was added to the colostrum feeds respectively up to the fourth feeds.
Figure 3:
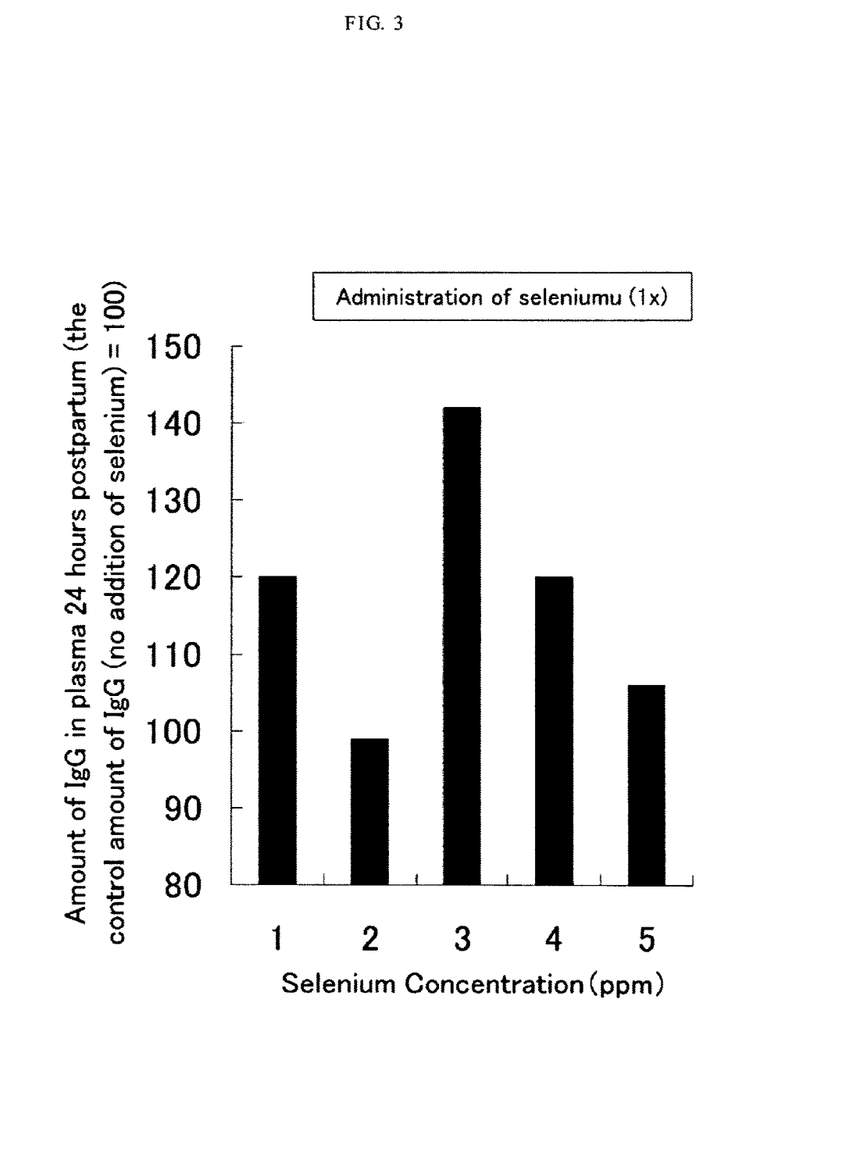
FIG. 3 is a comparative graph, which shows the IgG amount in plasma of calves administered with colostrum with selenium, in which 100 represents the IgG concentration in plasma of calves administered with colostrum without selenium. To calves administered with colostrum with selenium, selenium was added only to the first colostrum feeds.

In FIGS. 2 and 3, the results of the experiments are summarized. The IgG amount absorbed by of calves administered with colostrum without selenium was set to be 100, and in such scale, the IgG concentrations of calves administered with colostrum with selenium are shown in FIGS. 2 and 3. With respect to one set of experimental conditions, 3 to 6 pairs of calves were involved. The average values therefrom are shown in FIGS. 2 and 3.

As shown in FIGS. 2 and 3, in most of the experimental conditions, the IgG concentrations in plasma of the calves administered with colostrum added with selenium were shown to be higher than those of the calves administered with colostrum without selenium. The IgG concentration in plasma of the calves fed four times with colostrum with selenium was about the same level as those of the calves administered with colostrum with selenium for the first feeding and the rest without selenium. Accordingly, the above result suggests that the addition of selenium to colostrum after the second feeding is not particularly effective in enhancing the absorption of immunoglobulins in calves but does serves as a supplementary boost.

Figure 4:
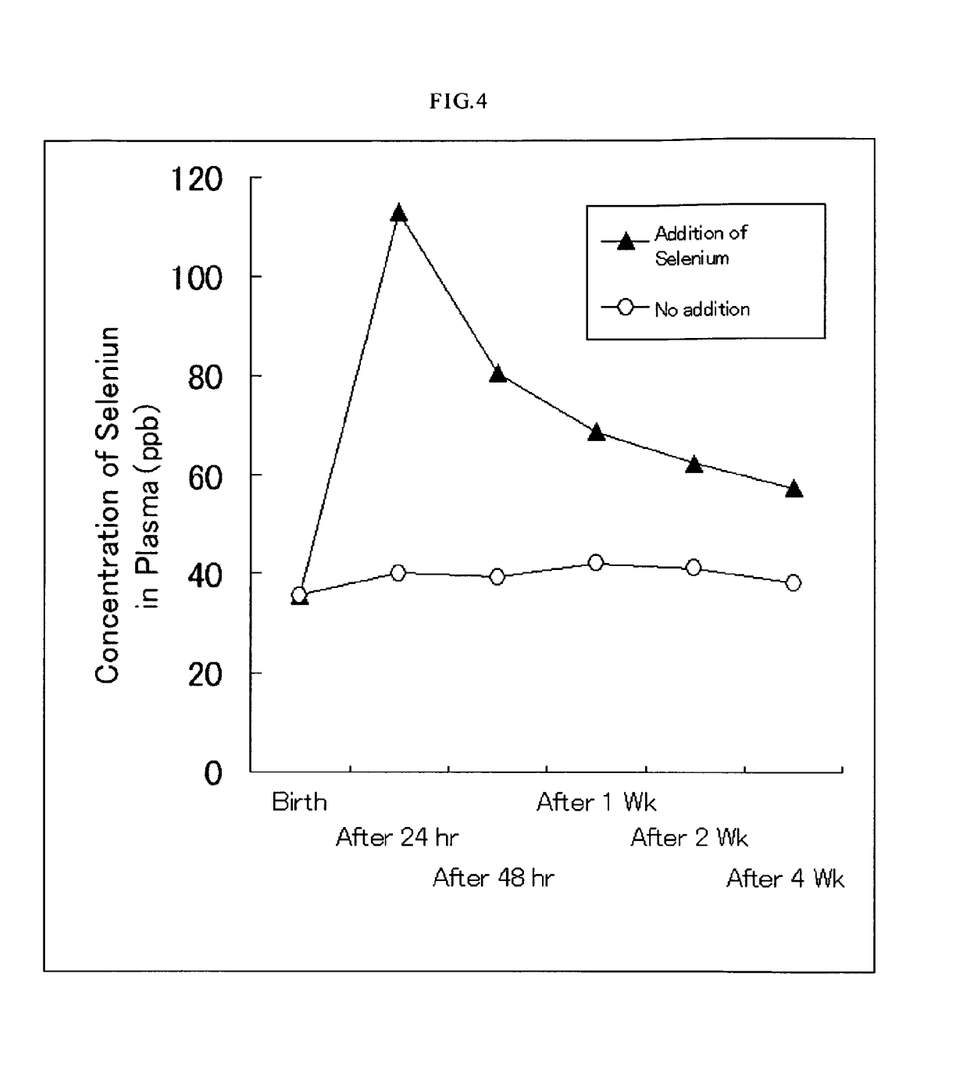
FIG. 4 is a comparative graph, which shows the selenium concentrations in plasma of calves fed with colostrum with or without selenium.

FIG. 4 shows temporal change of selenium level in blood at selenium level 3 ppm in FIG. 3. In comparison with the case of no addition of selenium, high selenium level in blood was maintained over 4 weeks postnatal by administration of selenium only once within 3 hours postnatal. Accordingly, enough amount of selenium is supplied by this method, and after that, it acts as essential minerals.

Figure 5:
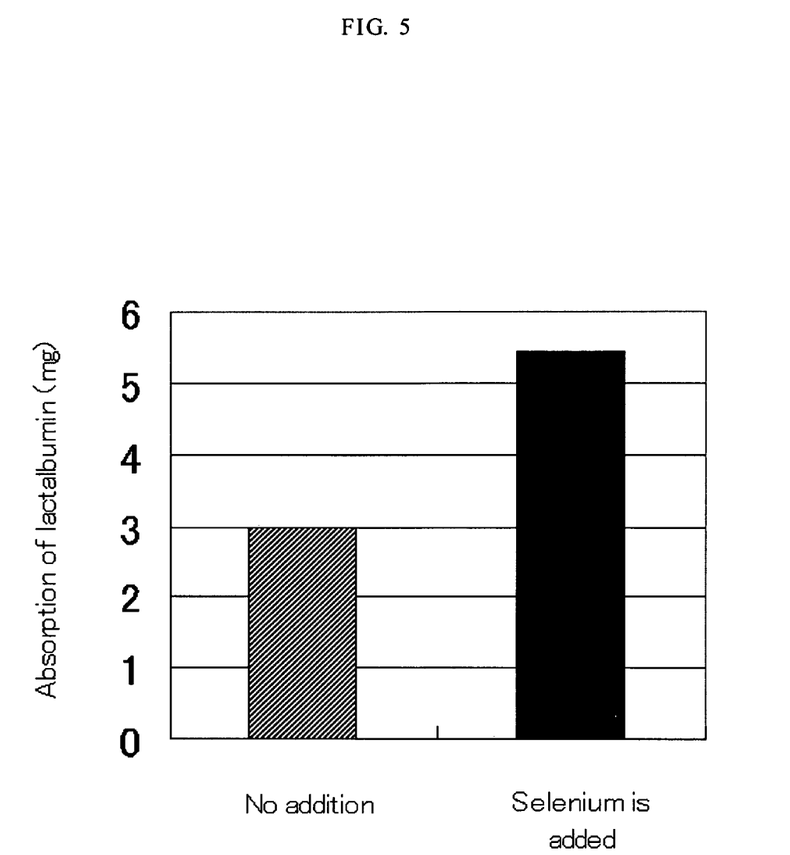
FIG. 5 is a comparative graph, which shows the lactalbumin in plasma of calves fed with colostrum with or without selenium. To calves administered with colostrum with selenium, selenium was added only to the first colostrum feeds.

FIG. 5 shows absorption of lactalbumin at 24 hours postnatal at selenium level 3 ppm in FIG. 3. In comparison with the case of no addition of selenium, addition of selenium enhances the absorption of lactalbumin. Therefore, selenium is effective in absorption of nonimmunoglobulin proteins such as lactalbumin. Accordingly, selenium enhances pinocytosis, thereby enhancing immunoglobulin proteins or nonimmunoglobulin proteins.

Figure 6:
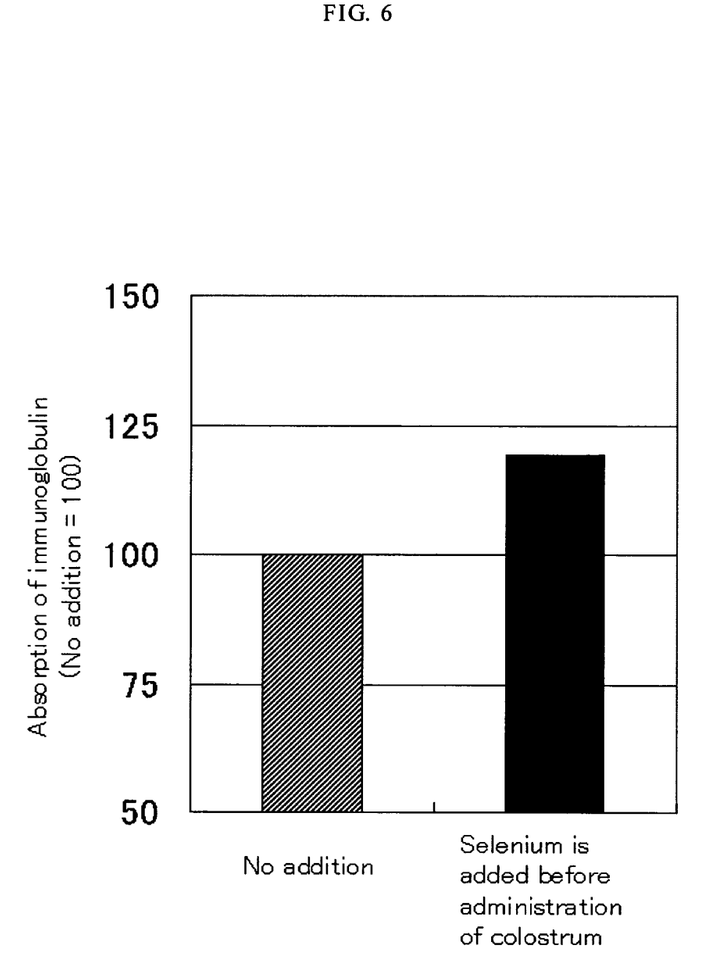
FIG. 6 is a comparative graph, which shows the IgG amount in plasma of calves fed with colostrum with or without selenium, in which 100 represents the IgG concentration changes in plasma of calves administered with colostrum without selenium.

FIG. 6 shows immunoglobulin G level in blood within 24 hours postnatal in cases where only 3 ppm selenium is administered within 2 hours postnatal, and after that, only colostrums is administered at 12 hours (2 L), 24 hours (2 L), and 36 hours (2 L) postnatal. In comparison with the case of no addition of selenium, absorption level of immunoglobulin G is high. Therefore, selenium is effective in absorption of immunoglobulin even if selenium and immunoglobulin protein are separately administered. Accordingly, selenium enhances pinocytosis without being mixed with immunoglobulin.

Figure 7:
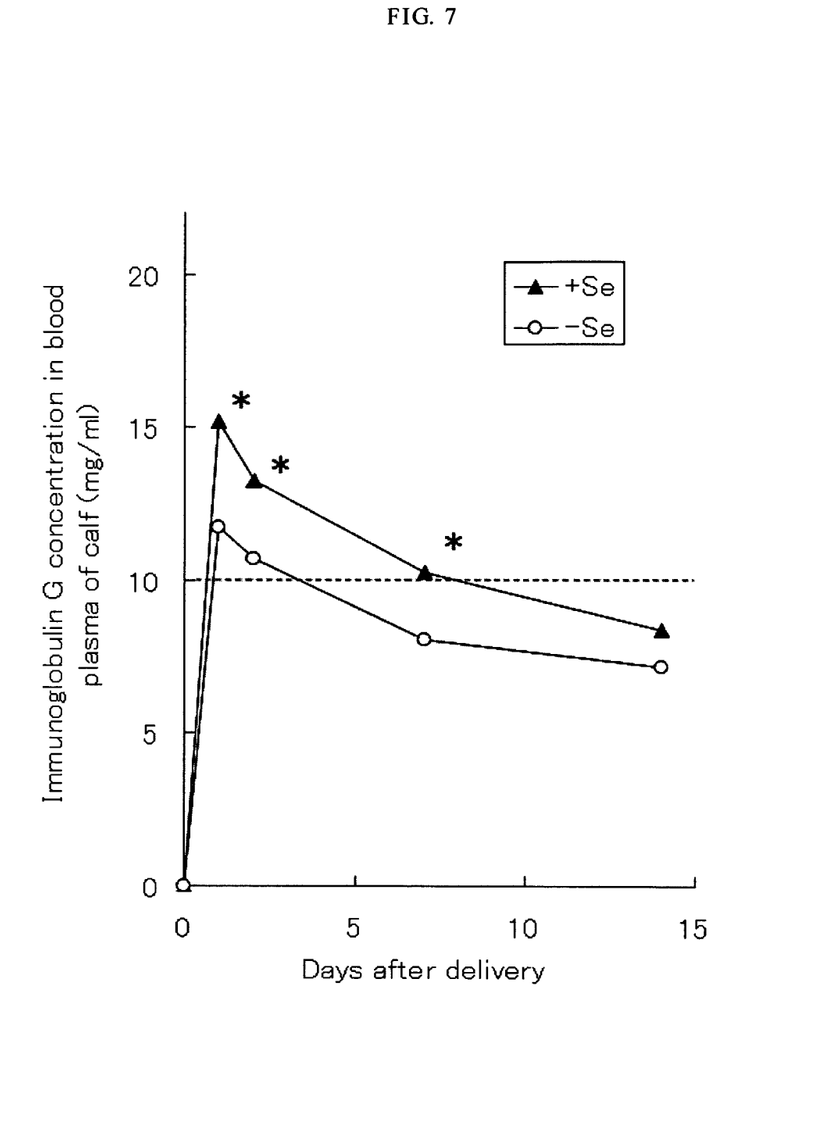
FIG. 7 is a comparative graph, which shows the IgG concentrations in plasma of calves fed with colostrum with or without selenium.

FIG. 7 shows temporal change of immunoglobulin G level in blood at selenium level 3 ppm in FIG. 3. In comparison with the case of no addition of selenium, immunoglobulin G level immediately after administration of selenium is high. Additionally, the high level against no addition was maintained over 14 days (2 weeks) after administration of selenium. Therefore, if much immunoglobulin can be absorbed in early stage after birth by administration of selenium, it is possible to maintain the high level of immunoglobulin G.

Moreover, the blood samples were taken 24, 48 hours and 1 week post-parturition respectively, and biochemical blood tests (with 18 factors) were carried out to investigate any adverse effects of added selenium on the health conditions of calves. There was little difference between the test results of the calves administered with colostrum added with selenium, and those of the calves administered with colostrum without selenium. Accordingly, there seems to be no adverse effects of added selenium on the health conditions of calves.

Accordingly, the present invention enables enhancement of immunity strength of postnatal calves and reduction of their attrition rates, thereby resulting in breeding of healthy milk cows and cattle.

From the foregoing it will be appreciated that, although specific embodiments have been described herein for purposes of illustration, various modifications may be made without deviating from the spirit and scope of the invention. Accordingly, the invention is not limited except as by the appended claims and the elements recited therein.

What is claimed is:

1. A method of enhancing immunoglobulin absorption efficiency in newborn calves, which comprises administering to a postnatal bovine within 12 hours postpartum an immunoglobulin feeding source comprising colostrum and a selenium compound, wherein the selenium is present at 2,000-5,000 µg selenium per liter of colostrum, and said administration involves one-time feeding of 1-2 liters of colostrum with said selenium compound.

2. The method of enhancing immunoglobulin absorption efficiency in a newborn calf according to claim 1, wherein said selenium is selected from the group consisting of one or more of sodium selenite, sodium selenate, potassium selenite, and potassium selenate.

\* \* \* \* \*